United States Patent [19]

Abramovitz et al.

[11] Patent Number: 5,728,808
[45] Date of Patent: Mar. 17, 1998

[54] HUMAN PROSTAGLANDIN RECEPTOR IP

[75] Inventors: Mark Abramovitz, Dollard de Ormeaux; Yves Bole, Outremont; Richard Grygorczyk, Dollard des Ormeaux; Kathleen Metters, Montreal, all of Canada; Thomas H. Rushmore, Hatfield, Pa.; Deborah M. Slipetz, Outremont, Canada

[73] Assignee: Merck Frosst Canada, Inc., Kirkland, Canada

[21] Appl. No.: 520,519

[22] Filed: Aug. 29, 1995

Related U.S. Application Data

[62] Division of Ser. No. 134,012, Oct. 6, 1993, Pat. No. 5,516,652.

[51] Int. Cl.$^6$ .................. C07K 14/705; C12N 15/09
[52] U.S. Cl. .................. 530/350; 435/691; 435/252.3; 435/254.11; 435/325
[58] Field of Search .................. 435/69.1, 325, 435/252.3, 254.11; 530/350, 395

[56] References Cited

PUBLICATIONS

R. Coleman, et al., Characterisation Of The Prostanoid Receptors Mediating Contraction of Guinea–Pig Isolated Trachea, (1985), Prostaglandins, 29, pp. 363–375.

P. Davies, et al., Prostaglandins and Inflammation, (1992), Inflammation: Basic Principles And Clinical Correlates, Gallin, Goldstein, Snyderman, eds., 2nd Ed., pp. 123–138.

E. Horton, et al., Uterine Luteolytic Hormone: A Physiological Role for Prostaglandin F2a, (1976), Physiol. Rev., 56, pp. 595–651.

D. DeWitt, Prostaglandin endoperoxide synthase: regulation of enzyme expression, (1991), Biochim. Biophys. Acta, 1083, pp. 121–134.

J. Stjernschantz, et al., Phenyl substituted prostaglandin analogs for glaucoma treatment, (1992), Drugs Future, 17, pp. 691–704.

P. Racz, et al., Maintained Intraocular Pressure Reduction With Once–a–Day Application of a New Prostaglandn F2a Analogue (PhXA41), (1993), Arch. Opthalmol., 111, pp. 657–661.

J. Senior, et al., In vitro characterization of prostandoid FP–, DP–, IP– and TP–receptors on the non–pregnant human myometrium, (1992), Brit. J. Pharmacol., 107, pp. 215–221.

J. Senior, et al., In vitro characterization of prostanoid receptors on human myometrium at term pregnancy, (1993), Brit. J. Pharmacol., 108, pp. 501–506.

J. Csepli, et al., The Effect Of The Prostaglandin F2a Analogue ICI 81008 On Uterine Small Arteries And On Blood Pressure, (1975), Prostaglandins, 10, pp. 689–697.

R. Coleman, Methods in prostanoid receptor classification, (1987), Prostaglandins And Related Substances—A Practical Approach, IRL Press, 1st Ed., pp. 267–303.

R. Coleman, et al., A study of the prostanoid receptors mediating bronchocorstriction in the anaesthetized guinea–pig and dog, (1981), Brit. J. Pharmacol., 74, p. 913.

J. Barnard, et al., Evaluation of prostaglandin F2a and prostacyclin interactions in the isolated perfused rat lung, (1992), J. Appl. Physiol., 72, pp. 2469–2474.

J. Davis, et al., Prostaglandin F2a stimulates phosphatidylinositol 4,5–bisphosphate hydrolysis and mobilizes intracellular Ca2+ in bovine luteal cells, (1987), Proc. Natl. Acad. Sci. U.S.A., 84, pp. 3728–3732.

J. Kitanaka, et al., Astrocytes Possess Prostaglandin F2a Receptors Coupled To Phospholipase C, (1991), Biochem. Biophys. Res. Comm., 178, pp. 946–952.

F. Black, et al., Activation of inositol phospholipid breakdown by prostaglandin F2a without any stimulation of prosferation in quiescent NIH–3T3 fibroblasts, (1990), Biochem. Journal, 266, pp. 661–667.

A. Nakao, et al., Characterization of Prostaglandin F2a Receptor of Mouse 3T3 Fibroblasts and its functional Expression in Xenopus Laevis Oocytes, (1993), J. Cell Physiol., 155, pp. 257–264.

W. Powell, et al., Prostaglandin F2a Receptor in Ovine corpora lutes, (1974), Eur. J. Biochem., 41, pp. 103–107.

W. Powell, et al., Occurrence and Properties of a Prostaglandin F2a Receptor in Bovine Corpora Lutea, (1975), Eur. J. Biochem., 56, pp. 73–77.

W. Powell, et al., Localization of a Prostaglandin F2a Receptor in BOvine Corpus luteum Plasma Membranes, (1976), Eur. J. Biochem., 61, pp. 605–611.

M. Molnar, et al., PGF$_2$a and PGE$_2$ binding to rat myometrium during gestation, parturition, and postpartum, (1990), Am. J. Physiol., 258, pp. E740–E747.

Th. Bauknecht, et al., Distribution of prostaglandin E2 and prostaglandin F2a receptors in human myometrium, (1981), Acta Endocrinol., 98, pp. 446–450.

F. Neuschafer–Rube, et al., Characterization of prostaglandin–F2a–binding sites on rat hepatocyte plasma membranes, 91993), Eur. J. Biochem., 211, pp. 163–169.

M. Hirata, et al., Cloning and expression of cDNA for a human thromboxane A2 receptor, (1991), Nature, 349, pp. 617–620.

A. Honda, et al., "Cloning and Expression of a cDNA for Mouse Prostaglandin E Receptor EP2 Subtype", (1993), J. Biol. Chem., 268, pp. 7759–7762.

Y. Sugimoto, et al., Two Isoforms of the EP$_3$ Receptor with Different Carboxyl–terminal Domains, (1993), J. Biol. Chem., 268, pp. 2712–2718.

Y. Sugimoto, et al., "Cloning and Expression of cDNA for Mouse Prostaglandin E Receptor EP3 Subtype", (1992), J. Biol. Chem., 267, pp. 6463–6466.

(List continued on next page.)

*Primary Examiner*—Sally P. Teng
*Attorney, Agent, or Firm*—J. Mark Hand; Jack L. Tribble

[57] ABSTRACT

A novel prostaglandin receptor has been identified and DNA encoding the receptor has been isolated, purified, sequenced and expressed in host cells. This DNA encoding the novel prostaglandin receptor and host cells expressing the receptor are used to identify modulators of the prostaglandin receptor.

6 Claims, 7 Drawing Sheets

OTHER PUBLICATIONS

K. Bunce, et al., Differential Effects Of Prostaglandins On Unidirectional Absorption And Secretion In Rat Ileum, (1987), Gastroenterology, 92, p. 1332.

Y. Dong, et al., Prostaglandin E receptor subtypes in smooth muscle: agonist activities of stable prostacyclin analogues, (1986), Br. J. Pharmacol., 87, pp. 97–107.

B. Hedqvist, et al., Prostaglandin–Induced Neurotransmission Failure In The Field–Stimulated, Isolated vas Deferens, (1972), Neuropharmacology, 11, pp. 177–187.

M. McKenniff, et al., Characterisation of receptors mediating the contractile effects of prostandoids in guinea–pig and human airways, (1988), Eur. J. Pharmacol., 153, pp. 149–159.

R. Eglen, et al., The action of prostanoid receptor agonists and antagonists on smooth muscle and platelets, (1988), Br. J. Pharmacol., 94, pp. 591–601.

J. Louttit, et al., Prostanoid EP–Receptors in Pig Saphenous vein, (7/26–31/92), 8th International Conf. on Prostaglandins, Abstract 258.

R. Lawrence, et al., Investigation of the prostaglandin E(EP–) receptor subtype mediating relaxation of the rabbit jugular vein, (1992), Br. J. Pharmacol., 105, pp. 817–824.

R. Coleman, et al., Prostanoids and their Receptors, (1989), Comprehensive Medicinal Chemistry, 3, pp. 643–714.

W. Campbell, et al., Lipid–Derived Autacoids: Eicosanoids And Platelet–Activating Factor, (1990), The Pharmacological Basis of Therapeutics, 8th Edition, pp. 600–617.

Adie, E.J. et al. Biochem. J., vol.285, pp. 529–536 (1992).

Masu et al. "cDNA cloning of bovine substance–K receptor through oocyte expression system", Nature, vol. 329, p. 836 (1987).

Tsai et al., J. Biol. Chem., 264, 61–67, 1989.

```
GATTCGTGCAGGAACCTCACCTACGTGCGGGCTCGGTGGGCCGCCACCAGCAC
CCTGATGTTCGTGGCCGGTGTGGGCTGGGCCCTGGGCCATCCTGAGCG
CACGGCGACCGGCGCCCCTTCGCGGTGCTGGTCACCGGACTGGCGGCC
ACCGACCTGCTGGGCACCAGCTTCCTGGCCCGTGTTCGTGGCCTATGCGCG
CAACAGCTCCCTGTGGGCTGGGCTGGCCCGAGGCGCCCCGTGCGATGCCTTCG
CCTTCGCCATGACCTTCTTCGGCCGTCATGCTCTTTGCCATGGCC
GTGGAGCGCGTGCCTGCGCTGAGCCACCCCTACGCCAGCTGACGGGCC
CCGCTGCGCCGCCCTGCCGCTGGCCAGCCATCTACGCCTTCTGCCTTCTGCG
CGCTGCCCCCTGCTGGGCCTGGGCCAACAGCAGTACTGCCCCGCAGCTGGTGC
TTCCTCCGCATGCGCTGTGGCCCTGCTGCATCTTCCTCTGCAACGCCTCGGTCACCC
CGGCCTGTGCTGCCGCAATGCCAGCAGGAAGCCACCAGGGCTCTGGTCCA
TCAGCCTCTGCCGCACCGGAGAGAGGTGGACCACCTGATCCTGCCCTCATGAC
CGGCCGCGCACCGGGGAGCGAGGTCCCCTGCTCCCTCACGATCCGCTTCACCAGGCTG
AGTGGTCATGGCCGTGTCCCTGACCGGGACCTCCCTTGCCTTCCGCTTCTACGCC
TCGCCCCTGACAGCAGCAGTGAGATGGGGACCCTGGGTCTTCATCCTTTTCCGCAAGGCTGTCTTCCA
TTCAACCCATCCTGGACTCTGGGTCTGCCCTGTGCCTGCCTGCCCACGGAGACTCGC
GCGACTCAAGCTCTGGTCTGCCCTGTGCCTGCCCGGCCTGCCCGGACCCCTCTGCT
AGACACACCCCTTTCCCAGCTCCCGGAGAGGGAGCTGCCTTTGTCGCGTGGAACGTCGTCCA
CCTGTGGGAAAGGAGGGAGCTGCCTTGGGCGGCCTGGGAACGTCGTCCA
GGAGCCCCTTGCCCTCCCCACACAGCAGTCCCCTGCTGACATTTCAAGCTGACCCTGTGA
AAGCAGAAGCCAGCCGTCGCCTGCCTCTGCTGACAGCCAGAAAATCAGGACATGGCTGATGGC
TCTCTGCCCCTTGCCCTTCGGCGACAGGAGCCAGAAACTCGGGCCGATCAGCTGCTTTCTC
TGCGGATGCTGGAACCTTGGCCCCAAACTCTGGGCCGATCAGCTGCTGTTTCTC
CTGCGGCCAGGGCAGTCGCTGCTGGAAGAGAGTGAGGGACAGAGAAACG
TTTATCCTGGAG  (SEQ.ID.NO.:5)
```

FIG. 1

```
GGCACAGACGCACGGGACAGGAGAGAGCCTGGGCAAGACTGGAGAGCCCAGACCTGGG
ATGGCGGATTCGTGCAGGAACCTCACCTACGTGCGGGGCTCGGTGGGCCGGCCAC
CAGCACCCTGATGTTCGTGCCGGTGGTGGGCAACGGCTGCCGGCCCTGGGCATCC
TGAGCGGCACGGCGCGGCCGACCTGCTCGGCGCCCTTCGCGCTGGTCACCGGACTG
GCGGCCACCGACCTGCTGGGCACCAGCTTCCTGAGCCCGGCCCGTGTTCGTGGCCTA
TGCGCGCAACAGCTCCCATGGGCCTGGGCCCGGAGGCGCCCCGCCCCTGTGCGATG
CCTTCGCCTTCGCCATGACCTTCTTCGCGCGTCCATGCTGTCCATCCTCTTTGCC
ATGGCCGTGGAGCGCTGCCTGGCGCTGAGCCGCTGCCAGCCACCCCTACCGCAGCTGGA
CGGGCCCCGCTGCGCCCGCTGGGCCCTGCCAGCCATCTACGCCTTCTGCGTCCTCT
TCTGCGCTGCCTGCCCCTGCTGGGCCCTGGGCCCTGTGGCTGCCATCTTCTCTGCTGGC
TGGTGCTTCCTCCGCATGCGCTGTGGCCCTGTGGCTGCCATCTTCCTCTGCAACGGCTCGG
CTACGCCGGCCTGGTGTGGCCCTGCTGGTGGCTGCCATCTTCCTCTGCAACGGCTCGG
TCACCCTCAGCCTCTGCCGCGATGTACCGCCAGCAGCGCACCAGGCTCTGCTCTG
GGTCCACGCGCCGCACCGGAGAGGACGAGGTGGACCACCTGATCCTGCTGCCCT
CATGACAGTGGTCATGCCCTGCTCCCTGCTGCCTCTCACGATCCGCTGCTTCACCC
AGGCTGTCGCCCCTGACAGCAGTGAGATGGGGGACCTTCCTTGCTCCGCTTC
TACGCCTTCAACCCCATCCTGGACCCCTGGGTCTTCATCCTTTTCCGCAAGGCTGT
CTTCATCCTTTTCCCGCAAGGCTGTGTCTTCCAGCGACTCAAGCTCTGGGGTCTGCC
TGTGCCTCGGGCCTGCCACGGAGACTCGCAGATCGCAGACACACCCTTCCCAGCTCGCCTCC
GGGAGGAGGACCCCAAGGGACCCCCAAGGCCCCTGTGGGCAGGTGGAGCCCTTGCCTCCCCACACAGT
GCCTTTGTCGGCTTGGGCCGTGGGAACGTCGTCCAAAGCAGAAGCCAGCGTCCCTGTCTTCGGCGACAGG
CCAGCGGCAGCGCCGTGACATTTCAAGCTGCATGGCCGGATGCTGGAACCTTGGCCCCCA
CTCTGCTGACATTTCAAGCTGCTGTTTCTCTGCGCCAGGCAGTGCCAGTCGCTGCTGGCT
AGCCAGAAAATCAGGAGGACATGGCTGTGTTTCTGCGGCAGTGCCAGGCAGTCGCTGCTGGCT
AACTCTGGGGCCGATCAGCTGCTGTTTCTGCGGCAGAGAAATGTTTATCCTGGAGTGCAGAAAGAATGG
CTGGAAGAGAGTGAGGGACAGAGAAATGTTTATCCTGGAGTGCAGAAAGAATGG
TTCTCTCAAAATAACCAGTGGCCTGGCCGACCCTGCTCTGGCC
(SEQ.ID.NO.:6)
```

FIG. 2

```
GGCACAGAGCGCACGGGACAGGAGAGCCTGGGCAAGACTGGAGAGCCCAGACCTGGG
ATGGCGGATTCGTCAGGAACCCTCACCTACGTGCGGGGCTCGGTGGGGCCGGCCAC
CAGCACCCTGATGTTCGTGCCGGTGTGGGCAACGGGCTGGCCTGGCCCTGGCATCC
TGAGCGCACGGCGACCGGCGCCCCCTCGGCCTTCGCGCGTTGCTGTCACCGGACTG
GCGCCACCGACCTGCTGGGCACAGTCCCTGGGCCTGCTGAGCCCGTGTTCGTGCCTA
TGCGCGCAACAGTCCCTGGGCCACCAGTTCTTGGGCCCGAGGCGGCCCGCCCTGTGCGATG
CCTTCGCCTTCGCCATGACCCTTCTTCGGCGTCCATGCTCCATCCTCTTTGCC
ATGGCCGTGGAGCGCTGCCCCCGCTGCCTGAGCGCTGACGCCCACCCTACCCTACGCGCAGCTGGA
CGGGCCCCTGCCCCCTGCTGGGCCTGGGCCCTGGGCCTAGCCCTCTGCTCCTCT
TCTGCGCGCTGCCTCCTCCGCATGCGCTGGGTGGCCCTGGTGGCCATCTTCCTGCAACGGCTCGG
CTACGCCCGGCTGGCTCTGCCGCGACCCTCTGCCATGTACCGCAGCAGCAGGGCTCCTG
TCACCCCTCAGCCTCGCCACCGGCACCGGAGACGGAGGACCACTTGCCTCTCCAGATCCTGTGGCCCT
GGTCCACGCCCACCGGAGACCGTGTGCCTCCGTGTGCCTCTCACGATCCGCTGCTTCACCC
CATGACAGTGGTCATGCCCTGACAGCAGCAGTGAGATGGGGACCTCCTTGCCTTCCGCTTC
AGGCTGTCGCCCCTGCAACCCCATCCTGACCCCTGGTCTTCATCCTTTTCCGCAAGGCTGT
TACGCCCTTCAACCCCATCCTGAGCTCTGCCTGTTCTGCCTGTCGCCTGCCCACGGAG
CTTCCAGCGACTCAAGCTCTGAAGCTCTGGTCTTCCCAGCTGCTGCCGGAGGAGGACCCAAGGCCCCC
ACTCGCAGAGACACCCCTTTCCCAGCTCCGGGAGCTGCCTTTGTCGCCGCCTTGGCGAGGG
TCTGCTCCTGTGGGGAAAGGAGGGCAGCCTCCCCACACAGTCCGCCTCCTCCAGCAGTCCGGCCGCCCGTGGGACGT
GCAGGTGGAGCCCTTGCCCTGTCTTGCCCTCGCGTCGCCAGCGTCCTCTCTGACATTCAAGCTGACC
CGTCCAAGAGCAGAAGCCAGCCCTCGCCTGTCTTCGGGCAAGGCCAGAATCAGGACATGGCT
CTGTGATCTCTGCCCTGGAACCTTGCTGCCCCCCAAACTCTGGGCCGATCAGCTGCTG
GATGGCTGCGCAGGGCAGTCGCTGGCCCAGGGCAGTCGCTGCTCTCTGGGAAGAGAGTGAGGGACAGAGG
TTTCTCTGGCAGGGCAGTCGCTGGCCTGGCTGCTGGGAAGAGAGTGAGGGACAGAGG
AAACGTTTATCCTGGAG   (SEQ. ID. NO.: 4)
```

FIG. 3

MADSCRNLTYVRGSVGPATSTLMFVAGVVGNGLALGLILSARRPARPSAFAVLVTGL
AATDLLGTSFLSPAVFVAYARNSSLLGLARGGPALCDAFAFAMTFFGLASMLILFA
MAVERCLALSHPYLYAQLDGPRCARLALPAIYAFCVLFCALPLLGLGQHQQYCPGS
WCFLRMRWAQPGGAAFSLAYAGLVALLVAAIFLCNGSVTLSLCRMYRQQKRHQGSL
GPRPRTGEDEVDHLILLALMTVVMAVCSLPLTIRCFTQAVAPDSSSEMGDLLAFRF
YAFNPILDPWVFILFRKAVFQRLKLWVCCLCLGPAHGDSQTPLSQLASGRRDPRAP
SAPVGKEGSCVPLSAWGEGQVEPLPPTQQSSGSAVGTSSKAEASVACSLC
(SEQ. ID. NO.:3)

FIG. 4

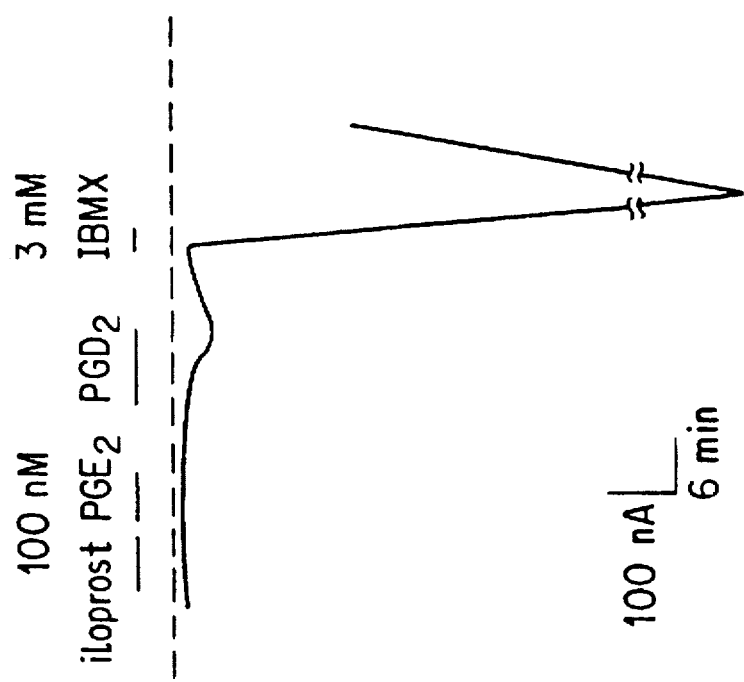

SEQUENCE LISTING ( 1 ) GENERAL INFORMATION:

( i i i ) NUMBER OF SEQUENCES: 6

( 2 ) INFORMATION FOR SEQ ID NO:1:

( i ) SEQUENCE CHARACTERISTICS:
        ( A ) LENGTH: 26 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:1:

TARATCCAGG GRTCYAGGAT GGGRTT 26

( 2 ) INFORMATION FOR SEQ ID NO:2:

( i ) SEQUENCE CHARACTERISTICS:
        ( A ) LENGTH: 9 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:2:

Asn Pro Ile Leu Asp Pro Trp Ile Tyr
1               5

( 2 ) INFORMATION FOR SEQ ID NO:3:

( i ) SEQUENCE CHARACTERISTICS:
        ( A ) LENGTH: 386 amino acids
        ( B ) TYPE: amino acid
        ( C ) STRANDEDNESS: single
        ( D ) TOPOLOGY: linear ( i i ) MOLECULE TYPE: protein ( x i ) SEQUENCE DESCRIPTION: SEQ ID NO:3:

Met Ala Asp Ser Cys Arg Asn Leu Thr Tyr Val Arg Gly Ser Val Gly
1               5                   10                  15

Pro Ala Thr Ser Thr Leu Met Phe Val Ala Gly Val Val Gly Asn Gly
                20                  25                  30

Leu Ala Leu Gly Ile Leu Ser Ala Arg Arg Pro Ala Arg Pro Ser Ala
            35                  40                  45

Phe Ala Val Leu Val Thr Gly Leu Ala Ala Thr Asp Leu Leu Gly Thr
    50                  55                  60

Ser Phe Leu Ser Pro Ala Val Phe Val Ala Tyr Ala Arg Asn Ser Ser
65                  70                  75                  80

Leu Leu Gly Leu Ala Arg Gly Gly Pro Ala Leu Cys Asp Ala Phe Ala
                85                  90                  95

Phe Ala Met Thr Phe Phe Gly Leu Ala Ser Met Leu Ile Leu Phe Ala
            100                 105                 110

| | | | | | | | | | | | | | |
|---|---|---|---|---|---|---|---|---|---|---|---|---|---|
| Met | Ala | Val<br>115 | Glu | Arg | Cys | Leu | Ala<br>120 | Leu | Ser | His | Pro | Tyr<br>125 | Leu | Tyr | Ala |
| Gln | Leu<br>130 | Asp | Gly | Pro | Arg | Cys<br>135 | Ala | Arg | Leu | Ala | Leu<br>140 | Pro | Ala | Ile | Tyr |
| Ala<br>145 | Phe | Cys | Val | Leu | Phe<br>150 | Cys | Ala | Leu | Pro | Leu<br>155 | Leu | Gly | Leu | Gly | Gln<br>160 |
| His | Gln | Gln | Tyr | Cys<br>165 | Pro | Gly | Ser | Trp | Cys<br>170 | Phe | Leu | Arg | Met | Arg<br>175 | Trp |
| Ala | Gln | Pro | Gly<br>180 | Gly | Ala | Ala | Phe | Ser<br>185 | Leu | Ala | Tyr | Ala | Gly<br>190 | Leu | Val |
| Ala | Leu | Leu<br>195 | Val | Ala | Ala | Ile | Phe<br>200 | Leu | Cys | Asn | Gly | Ser<br>205 | Val | Thr | Leu |
| Ser | Leu<br>210 | Cys | Arg | Met | Tyr | Arg<br>215 | Gln | Gln | Lys | Arg | His<br>220 | Gln | Gly | Ser | Leu |
| Gly<br>225 | Pro | Arg | Pro | Arg | Thr<br>230 | Gly | Glu | Asp | Glu | Val<br>235 | Asp | His | Leu | Ile | Leu<br>240 |
| Leu | Ala | Leu | Met | Thr<br>245 | Val | Val | Met | Ala | Val<br>250 | Cys | Ser | Leu | Pro | Leu<br>255 | Thr |
| Ile | Arg | Cys | Phe<br>260 | Thr | Gln | Ala | Val | Ala<br>265 | Pro | Asp | Ser | Ser | Ser<br>270 | Glu | Met |
| Gly | Asp | Leu<br>275 | Leu | Ala | Phe | Arg | Phe<br>280 | Tyr | Ala | Phe | Asn | Pro<br>285 | Ile | Leu | Asp |
| Pro | Trp<br>290 | Val | Phe | Ile | Leu | Phe<br>295 | Arg | Lys | Ala | Val | Phe<br>300 | Gln | Arg | Leu | Lys |
| Leu<br>305 | Trp | Val | Cys | Cys | Leu<br>310 | Cys | Leu | Gly | Pro | Ala<br>315 | His | Gly | Asp | Ser | Gln<br>320 |
| Thr | Pro | Leu | Ser | Gln<br>325 | Leu | Ala | Ser | Gly | Arg<br>330 | Arg | Asp | Pro | Arg | Ala<br>335 | Pro |
| Ser | Ala | Pro | Val<br>340 | Gly | Lys | Glu | Gly | Ser<br>345 | Cys | Val | Pro | Leu | Ser<br>350 | Ala | Trp |
| Gly | Glu | Gly<br>355 | Gln | Val | Glu | Pro | Leu<br>360 | Pro | Pro | Thr | Gln | Gln<br>365 | Ser | Ser | Gly |
| Ser | Ala<br>370 | Val | Gly | Thr | Ser | Ser<br>375 | Lys | Ala | Glu | Ala | Ser<br>380 | Val | Ala | Cys | Ser |
| Leu<br>385 | Cys | | | | | | | | | | | | | | |

( 2 ) INFORMATION FOR SEQ ID NO:4:

( i ) SEQUENCE CHARACTERISTICS:
        ( A ) LENGTH: 1417 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:4:

```
GGCACAGACG CACGGGACAG GAGAGCCTGG GCAAGACTGG AGAGCCCAGA CCTGGGATGG      60
CGGATTCGTG CAGGAACCTC ACCTACGTGC GGGGCTCGGT GGGGCCGGCC ACCAGCACCC     120
TGATGTTCGT GGCCGGTGTG GTGGGCAACG GGCTGGCCCT GGGCATCCTG AGCGCACGGC     180
GACCGGCGCG CCCCTCGGCC TTCGCGGTGC TGGTCACCGG ACTGGCGGCC ACCGACCTGC     240
TGGGCACCAG CTTCCTGAGC CCGGCCGTGT TCGTGGCCTA TGCGCGCAAC AGCTCCCTGC     300
TGGGCCTGGC CCGAGGCGGC CCCGCCCTGT GCGATGCCTT CGCCTTCGCC ATGACCTTCT     360
TCGGCCTGGC GTCCATGCTC ATCCTCTTTG CCATGGCCGT GGAGCGCTGC CTGGCGCTGA     420
```

```
GCCACCCCTA CCTCTACGCG CAGCTGGACG GGCCCCGCTG CGCCCGCCTG GCGCTGCCAG        480

CCATCTACGC CTTCTGCGTC CTCTTCTGCG CGCTGCCCCT GCTGGGCCTG GGCCAACACC        540

AGCAGTACTG CCCCGGCAGC TGGTGCTTCC TCCGCATGCG CTGGGCCCAG CCGGGCGGCG        600

CCGCCTTCTC GCTGGCCTAC GCCGGCCTGG TGGCCCTGCT GGTGGCTGCC ATCTTCCTCT        660

GCAACGGCTC GGTCACCCTC AGCCTCTGCC GCATGTACCG CCAGCAGAAG CGCCACCAGG        720

GCTCTCTGGG TCCACGGCCG CGCACCGGAG AGGACGAGGT GGACCACCTG ATCCTGCTGG        780

CCCTCATGAC AGTGGTCATG GCCGTGTGCT CCCTGCCTCT CACGATCCGC TGCTTCACCC        840

AGGCTGTCGC CCCTGACAGC AGCAGTGAGA TGGGGGACCT CCTTGCCTTC CGCTTCTACG        900

CCTTCAACCC CATCCTGGAC CCCTGGGTCT TCATCCTTTT CCGCAAGGCT GTCTTCCAGC        960

GACTCAAGCT CTGGGTCTGC TGCCTGTGCC TCGGGCCTGC CCACGGAGAC TCGCAGACAC       1020

CCCTTTCCCA GCTCGCCTCC GGGAGGAGGG ACCCAAGGGC CCCCTCTGCT CCTGTGGGAA       1080

AGGAGGGGAG CTGCGTGCCT TTGTCGGCTT GGGGCGAGGG GCAGGTGGAG CCCTTGCCTC       1140

CCACACAGCA GTCCAGCGGC AGCGCCGTGG GAACGTCGTC CAAAGCAGAA GCCAGCGTCG       1200

CCTGCTCCCT CTGCTGACAT TTCAAGCTGA CCCTGTGATC TCTGCCCTGT CTTCGGGCGA       1260

CAGGAGCCAG AAAATCAGGG ACATGGCTGA TGGCTGCGGA TGCTGGAACC TTGGCCCCCA       1320

AACTCTGGGG CCGATCAGCT GCTGTTTCTC TGCGGCAGGG CAGTCGCTGC TGGCTCTGGG       1380

AAGAGAGTGA GGGACAGAGG AAACGTTTAT CCTGGAG                                1417
```

( 2 ) INFORMATION FOR SEQ ID NO:5:

( i ) SEQUENCE CHARACTERISTICS:
        ( A ) LENGTH: 1356 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:5:

```
GATTCGTGCA GGAACCTCAC CTACGTGCGG GGCTCGGTGG GGCCGGCCAC CAGCACCCTG         60

ATGTTCGTGG CCGGTGTGGT GGGCAACGGG CTGGCCCTGG GCATCCTGAG CGCACGGCGA        120

CCGGCGCGCC CCTCGGCCTT CGCGGTGCTG GTCACCGGAC TGGCGGCCAC CGACCTGCTG        180

GGCACCAGCT TCCTGAGCCC GGCCGTGTTC GTGGCCTATG CGCGCAACAG CTCCCTGCTG        240

GGCCTGGCCC GAGGCGGCCC CGCCCTGTGC GATGCCTTCG CCTTCGCCAT GACCTTCTTC        300

GGCCTGGCGT CCATGCTCAT CCTCTTTGCC ATGGCCGTGG AGCGCTGCCT GGCGCTGAGC        360

CACCCCTACC TCTACGCGCA GCTGGACGGG CCCGCTGCG CCCGCCTGGC GCTGCCAGCC         420

ATCTACGCCT TCTGCGTCCT CTTCTGCGCG CTGCCCCTGC TGGGCCTGGG CCAACACCAG        480

CAGTACTGCC CCGGCAGCTG GTGCTTCCTC CGCATGCGCT GGGCCCAGCC GGGCGGCGCC        540

GCCTTCTCGC TGGCCTACGC CGGCCTGGTG GCCCTGCTGG TGGCTGCCAT CTTCCTCTGC        600

AACGGCTCGG TCACCCTCAG CCTCTGCCGC ATGTACCGCC AGCAGAAGCG CCACCAGGGC        660

TCTCTGGGTC CACGGCCGCG CACCGGAGAG GACGAGGTGG ACCACCTGAT CCTGCTGGCC        720

CTCATGACAG TGGTCATGGC CGTGTGCTCC CTGCCTCTCA CGATCCGCTG CTTCACCCAG        780

GCTGTCGCCC CTGACAGCAG CAGTGAGATG GGGGACCTCC TTGCCTTCCG CTTCTACGCC        840

TTCAACCCCA TCCTGGACCC CTGGGTCTTC ATCCTTTTCC GCAAGGCTGT CTTCCAGCGA        900

CTCAAGCTCT GGGTCTGCTG CCTGTGCCTC GGGCCTGCCC ACGGAGACTC GCAGACACCC        960
```

-continued

| | | | | | |
|---|---|---|---|---|---|
| CTTTCCCAGC | TCGCCTCCGG | GAGGAGGGAC | CCAAGGGCCC | CCTCTGCTCC | TGTGGGAAAG | 1020 |
| GAGGGAGCT | GCGTGCCTTT | GTCGGCTTGG | GGCGAGGGGC | AGGTGGAGCC | CTTGCCTCCC | 1080 |
| ACACAGCAGT | CCAGCGGCAG | CGCCGTGGGA | ACGTCGTCCA | AAGCAGAAGC | CAGCGTCGCC | 1140 |
| TGCTCCCTCT | GCTGACATTT | CAAGCTGACC | CTGTGATCTC | TGCCCTGTCT | TCGGGCGACA | 1200 |
| GGAGCCAGAA | AATCAGGGAC | ATGGCTGATG | GCTGCGGATG | CTGGAACCTT | GGCCCCAAA | 1260 |
| CTCTGGGGCC | GATCAGCTGC | TGTTTCTCCT | GCGGCAGGGC | AGTCGCTGCT | GGCTCTGGGA | 1320 |
| AGAGAGTGAG | GGACAGAGGA | AACGTTTATC | CTGGAG | | | 1356 |

( 2 ) INFORMATION FOR SEQ ID NO:6:

( i ) SEQUENCE CHARACTERISTICS:
        ( A ) LENGTH: 1498 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:6:

| | | | | | |
|---|---|---|---|---|---|
| GGCACAGACG | CACGGGACAG | GAGAGCCTGG | GCAAGACTGG | AGAGCCCAGA | CCTGGGATGG | 60 |
| CGGATTCGTG | CAGGAACCTC | ACCTACGTGC | GGGGCTCGGT | GGGGCCGGCC | ACCAGCACCC | 120 |
| TGATGTTCGT | GGCCGGTGTG | GTGGGCAACG | GCTGGCCCT | GGCATCCTG | AGCGCACGGC | 180 |
| GACCGGCGCG | CCCCTCGGCC | TTCGCGGTGC | TGGTCACCGG | ACTGGCGGCC | ACCGACCTGC | 240 |
| TGGGCACCAG | CTTCCTGAGC | CCGGCCGTGT | TCGTGGCCTA | TGCGCGCAAC | AGCTCCCTGC | 300 |
| TGGGCCTGGC | CCGAGGCGGC | CCCGCCCTGT | GCGATGCCTT | CGCCTTCGCC | ATGACCTTCT | 360 |
| TCGGCCTGGC | GTCCATGCTC | ATCCTCTTTG | CCATGGCCGT | GGAGCGCTGC | CTGGCGCTGA | 420 |
| GCCACCCCTA | CCTCTACGCG | CAGCTGGACG | GGCCCCGCTG | CGCCCGCCTG | GCGCTGCCAG | 480 |
| CCATCTACGC | CTTCTGCGTC | CTCTTCTGCG | CGCTGCCCCT | GCTGGGCCTG | GCCAACACC | 540 |
| AGCAGTACTG | CCCCGGCAGC | TGGTGCTTCC | TCCGCATGCG | CTGGGCCCAG | CCGGGCGGCG | 600 |
| CCGCCTTCTC | GCTGGCCTAC | GCCGGCCTGG | TGGCCCTGCT | GGTGGCTGCC | ATCTTCCTCT | 660 |
| GCAACGGCTC | GGTCACCCTC | AGCCTCTGCC | GCATGTACCG | CCAGCAGAAG | CGCCACCAGG | 720 |
| GCTCTCTGGG | TCCACGGCCG | CGCACCGGAG | AGGACGAGGT | GGACCACCTG | ATCCTGCTGG | 780 |
| CCCTCATGAC | AGTGGTCATG | GCCGTGTGCT | CCCTGCCTCT | CACGATCCGC | TGCTTCACCC | 840 |
| AGGCTGTCGC | CCCTGACAGC | AGCAGTGAGA | TGGGGGACCT | CCTTGCCTTC | CGCTTCTACG | 900 |
| CCTTCAACCC | CATCCTGGAC | CCCTGGGTCT | TCATCCTTTT | CCGCAAGGCT | GTCTTCATCC | 960 |
| TTTTCCGCAA | GGCTGTCTTC | CAGCGACTCA | AGCTCTGGGT | CTGCTGCCTG | GCCTCGGGC | 1020 |
| CTGCCCACGG | AGACTCGCAG | ACACCCCTTT | CCCAGCTCGC | CTCCGGGAGG | AGGGACCCAA | 1080 |
| GGGCCCCCTC | TGCTCCTGTG | GGAAGGAGG | GGAGCTGCGT | GCCTTTGTCG | GCTTGGGGCG | 1140 |
| AGGGCAGGT | GGAGCCCTTG | CCTCCCACAC | AGCAGTCCAG | CGGCAGCGCC | GTGGGAACGT | 1200 |
| CGTCCAAAGC | AGAAGCCAGC | GTCGCCTGCT | CCCTCTGCTG | ACATTTCAAG | CTGACCCTGT | 1260 |
| GATCTCTGCC | CTGTCTTCGG | GCGACAGGAG | CCAGAAAATC | AGGGACATGG | CTGATGGCTG | 1320 |
| CGGATGCTGG | AACCTTGGCC | CCCAAACTCT | GGGGCCGATC | AGCTGCTGTT | TCTCCTGCGG | 1380 |
| CAGGGCAGTC | GCTGCTGGCT | CTGGGAAGAG | AGTGAGGGAC | AGAGGAAATG | TTTATCCTGG | 1440 |
| AGTGCAGAAA | GAATGGTTCT | CTCAAAATAA | CCAGTGGCCT | GGCCGACCTG | CTCTGGCC | 1498 |

HUMAN PROSTAGLANDIN RECEPTOR IP

This is a division of application Ser. No. 08/134,012 filed Oct. 6, 1993, now U.S. Pat. No. 5,516,652.

BACKGROUND OF THE INVENTION $PGI_2$ causes relaxation of arterial smooth muscle and inhibition of platelet aggregation, degranulation and shape change and is, therefore, thought to be important in maintaining vascular homeostasis. Other potential roles for $PGI_2$ are not well established but include regulation of renal blood flow, renin release and glomerular filtration rate in the kidney cortex, modulation of neurotransmitter release in the heart and stimulation of secretion in the stomach and large intestine. In common with the other prostaglandins, $PGI_2$ is also involved in the inflammatory response eliciting hyperaemia, edema, hyperanalgesia and pyrexia primarily through its role as a vasodilator.

The physiological actions of prostaglandin $(PG)I_2$ are mediated through interaction with the prostaglandin IP receptor. The known distribution of IP receptors is reflective of the physiological actions of $PGI_2$. They have been extensively characterized by radioligand binding studies in platelets from many species including human and identified in pharmacological studies as present in coronary, pulmonary, renal and several other arterial preparations as well as the heart. IP receptors may also be present in myometrium, penile erectile tissue and the iris sphincter muscle and have been reported in the NCB-20 and NG108-15 neuronal hybrid cell lines and the mouse mastocytoma P-815 cell line.

Functional activities of the IP receptor have been studied using tissue preparations such as arterial smooth muscle and cell based assays using platelets. The above methods for studying IP receptor activities have several disadvantages in that they require preparations containing several different but related receptor populations, with different ligand binding properties, making measurements of absolute potency and selectivity very difficult. In addition, tissues contain varying levels of IP receptor and since tissue samples are required, compounds cannot satisfactorily be tested as effectors of the human IP receptor.

SUMMARY OF THE INVENTION

A novel prostaglandin receptor protein termed IP has been identified from human cells. A DNA molecule encoding the full length IP protein has been isolated and purified, and the nucleotide sequence has been determined. The IP encoding DNA has been cloned into expression vectors and these expression vectors, when introduced into recombinant host cells, cause the recombinant host cells to express a functional IP receptor protein. The novel IP protein, the IP-encoding DNA, the expression vectors and recombinant host cells expressing recombinant IP are useful in the identification of modulators of IP receptor activity.

A method of identifying IP receptor modulators is also disclosed which utilizes the recombinant IP expressing host cells. Modulators of IP activity are useful for the treatment of prostaglandin-related diseases and for modulating the effects of prostaglandins on the IP receptor.

BRIEF DESCRIPTION OF THE DRAWINGS

FIG. 1—The DNA sequence of human IP cDNA clone hLXR3-6 is shown.

FIG. 2—The DNA sequence of human IP cDNA clone hLXR3-11 is shown.

FIG. 3—The DNA sequence human IP cDNA construct 11/6hLXR3 encoding the IP receptor protein is shown.

FIG. 4—The complete deduced amino acid sequence of the IP receptor protein encoded by 11/6hLXR3 is shown.

The voltage-clamp experiments shown here were performed 48 hr after nuclear injection and are representative of 6 separate experiments with oocytes from 3 different frogs.

Figure 6:
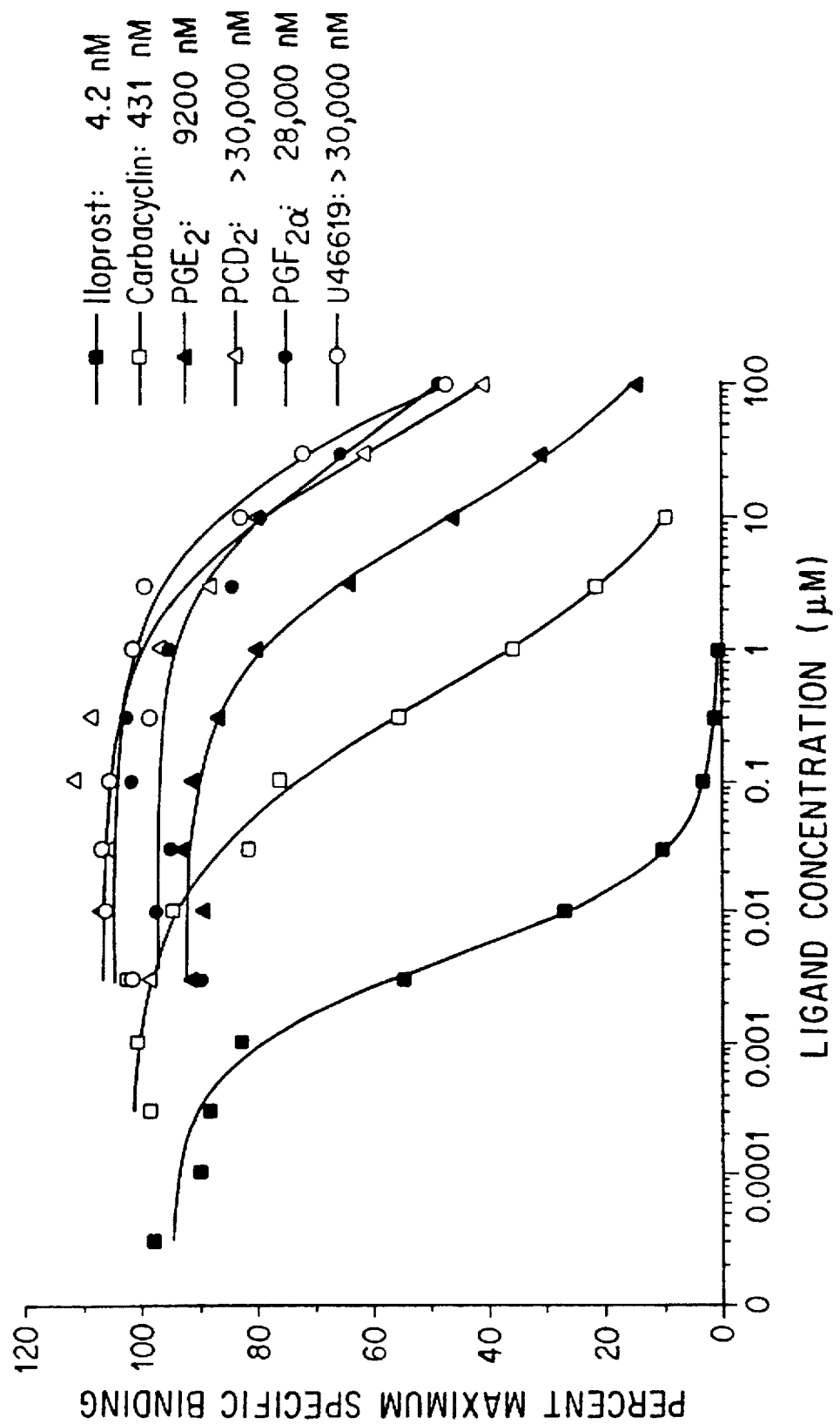

FIG. 6—Competition for [$^3$H]-iloprost specific binding to pcDNAIamp-hIP transfected COS-M6 membranes. [$^3$H] Iloprost binding assays were performed as described in Example 7. The percentage maximum [$^3$H]iloprost specific binding at each competing ligand concentration was determined for iloprost (■), the stable IP receptor agonist carbacyclin (□), $PGE_2$ (▲), $PGF_{2\alpha}$ (●), $PGD_2$ (△) and the TP-receptor agonist U46619 (○), over a concentration range up to 100 mM.

DETAILED DESCRIPTION OF THE INVENTION

The present invention relates to cDNA encoding a novel prostaglandin receptor, termed IP. The present invention is also related to recombinant host cells which express the cloned IP-encoding DNA contained in a recombinant expression plasmid. The present invention is also related to methods for the screening of substances which modulate IP receptor activity. The DNA of the present invention is isolated from IP producing cells. IP, as used herein, refers to a G protein-coupled receptor which can specifically bind prostaglandin molecules.

Mammalian cells capable of producing IP include, but are not limited to, cells derived from the small and large intestine, kidney, stomach, vascular smooth muscle, eye, placenta, uterus, thymus and platelets. Transformed mammalian cell lines which produce IP include, but are not limited to, mastocytoma P-815 cells. The preferred cells for the present invention include normal human kidney and platelets and the most preferred cells are human lung cells.

Other cells and cell lines may also be suitable for use to isolate IP cDNA. Selection of suitable cells may be done by screening for IP on cell surfaces. Methods for detecting IP activity are well known in the art and measure the binding of radiolabelled ligand specific for the receptor. Cells which possess IP activity in this assay may be suitable for the isolation of IP cDNA.

Any of a variety of procedures may be used to clone IP cDNA. These methods include, but are not limited to, direct functional expression of the IP cDNA following the construction of an IP-containing cDNA library in an appropriate expression vector system. Another method is to screen an IP-containing cDNA library constructed in a bacteriophage or plasmid shuttle vector with a labelled oligonucleotide probe designed from the amino acid sequence of the IP protein. The preferred method consists of screening an IP-containing cDNA library constructed in a bacteriophage or plasmid shuttle vector with a partial cDNA encoding the IP protein. This partial cDNA is obtained by the specific PCR amplification of IP DNA fragments through the design of degenerate oligonucleotide primers from the amino acid sequence known for other G protein-coupled receptors which are related to the prostaglandin IP receptors.

It is readily apparent to those skilled in the art that other types of libraries, as well as libraries constructed from other cells or cell types, may be useful for isolating IP-encoding DNA. Other types of libraries include, but are not limited to, cDNA libraries derived from other cells or cell lines and genomic DNA libraries.

It is readily apparent to those skilled in the art that suitable cDNA libraries may be prepared from cells or cell lines which have IP activity. The selection of cells or cell lines for use in preparing a cDNA library to isolate IP cDNA may be done by first measuring cell associated IP activity using the known labelled ligand binding assay cited above and used herein.

Preparation of cDNA libraries can be performed by standard techniques well known in the art. Well known cDNA library construction techniques can be found for example, in Maniatis, T., Fritsch, E. F., Sambrook, J., Molecular Cloning: A Laboratory Manual (Cold Spring Harbor Laboratory, Cold Spring Harbor, N.Y., 1982).

It is also readily apparent to those skilled in the art that DNA encoding IP may also be isolated from a suitable genomic DNA library. Construction of genomic DNA libraries can be performed by standard techniques well known in the art. Well known genomic DNA library construction techniques can be found in Maniatis, T., Fritsch, E. F., Sambrook, J. in Molecular Cloning: A Laboratory Manual (Cold Spring Harbor Laboratory, Cold Spring Harbor, N.Y., 1982).

In order to clone the IP gene by one of the preferred methods, the amino acid sequence or DNA sequence of IP or a homologous protein is necessary. To accomplish this, IP protein or a homologous protein may be purified and partial amino acid sequence determined by automated sequenators. It is not necessary to determine the entire amino acid sequence, but the linear sequence of two regions of 6 to 8 amino acids can be determined for the PCR amplification of a partial IP DNA fragment.

Once suitable amino acid sequences have been identified, the DNA sequences capable of encoding them are synthesized. Because the genetic code is degenerate, more than one codon may be used to encode a particular amino acid, and therefore, the amino acid sequence can be encoded by any of a set of similar DNA oligonucleotides. Only one member of the set will be identical to the IP sequence but others in the set will be capable of hybridizing to IP DNA even in the presence of DNA oligonucleotides with mismatches. The mismatched DNA oligonucleotides may still sufficiently hybridize to the IP DNA to permit identification and isolation of IP encoding DNA.

Using one of the preferred methods, cDNA clones encoding IP are isolated in a two-stage approach employing polymerase chain reaction (PCR) based technology and cDNA library screening. In the first stage, NH$_2$-terminal and internal amino acid sequence information from the purified IP or a homologous protein is used to design degenerate oligonucleotide primers for the amplification of IP-specific DNA fragments. In the second stage, these fragments are cloned to serve as probes for the isolation of full length cDNA from cDNA libraries.

The sequence for the cDNA encoding IP is shown in Table 1, and was designated clone 11/6hLXR3. The deduced amino acid sequence of IP from the cloned cDNA is shown in Table 2. Inspection of the determined cDNA sequence reveals the presence of a single, large open reading frame that encodes for a 386 amino acid protein.

The cloned IP cDNA obtained through the methods described above may be recombinantly expressed by molecular cloning into an expression vector containing a suitable promoter and other appropriate transcription regulatory elements, and transferred into prokaryotic or eukaryotic host cells to produce recombinant IP. Techniques for such manipulations can be found described in Maniatis, T, et al., supra, and are well known in the art.

Expression vectors are defined herein as DNA sequences that are required for the transcription of cloned DNA and the translation of their mRNAs in an appropriate host. Such vectors can be used to express eukaryotic DNA in a variety of hosts such as bacteria, bluegreen algae, plant cells, insect cells and animal cells.

Specifically designed vectors allow the shuttling of DNA between hosts such as bacteria-yeast or bacteria-animal cells. An appropriately constructed expression vector should contain: an origin of replication for autonomous replication in host cells, selectable markers, a limited number of useful restriction enzyme sites, a potential for high copy number, and active promoters. A promoter is defined as a DNA sequence that directs RNA polymerase to bind to DNA and initiate RNA synthesis. A strong promoter is one which causes mRNAs to be initiated at high frequency. Expression vectors may include, but are not limited to, cloning vectors, modified cloning vectors, specifically designed plasmids or viruses.

A variety of mammalian expression vectors may be used to express recombinant IP in mammalian cells. Commercially available mammalian expression vectors which may be suitable for recombinant IP expression, include but are not limited to, pMC1neo (Stratagene), pXT1 (Stratagene), pSG5 (Stratagene), pcDNAI, pcDNAIamp (Invitrogen), EBO-pSV2-neo (ATCC 37593)pBPV-1(8-2) (ATCC 37110), pdBPV-MMTneo(342-12) (ATCC 37224), pRS-Vgpt (ATCC 37199), pRSVneo (ATCC 37198), pSV2-dhfr (ATCC 37146), pUCTag (ATCC 37460), 1ZD35 (ATCC 37565), and vaccinia virus transfer vector pTM1.

DNA encoding IP may also be cloned into an expression vector for expression in a host cell. Host cells may be prokaryotic or eukaryotic, including but not limited to bacteria, yeast, mammalian cells including but not limited to cell lines of human, bovine, porcine, monkey and rodent origin, and insect cells including but not limited to Sf9 and drosophila derived cell lines. Cell lines derived from mammalian species which may be suitable and which are commercially available, include but are not limited to, CV-1 (ATCC CCL 70), COS-1 (ATCC CRL 1650), COS-7 (ATCC CRL 1651), CHO-K1 (ATCC CCL 61), 3T3 (ATCC CCL 92), NIH/3T3 (ATCC CRL 1658), HeLa (ATCC CCL 2), C127I (ATCC CRL 1616), BS-C-1 (ATCC CCL 26) and MRC-5 (ATCC CCL 171).

The expression vector may be introduced into host cells via any one of a number of techniques including but not limited to transformation, transfection, infection, protoplast fusion, and electroporation. The expression vector-containing cells are individually analyzed to determine whether they produce IP protein. Identification of IP expressing cells may be done by several means, including but not limited to immunological reactivity with anti-IP antibodies, and the presence of host cell-associated IP activity.

Expression of IP DNA may also be performed using in vitro produced synthetic mRNA. Synthetic mRNA can be efficiently translated in various cell-free systems, including but not limited to wheat germ extracts and reticulocyte extracts, as well as efficiently translated in cell based systems, including but not limited to microinjection into frog oocytes, with microinjection into frog oocytes being preferred.

To determine the IP cDNA sequence(s) that yields optimal levels of receptor activity and/or IP protein, IP cDNA molecules including but not limited to the following can be constructed: the full-length open reading frame of the IP cDNA and various constructs containing portions of the cDNA encoding only specific domains of the receptor protein or rearranged domains of the protein. All constructs can be designed to contain none, all or portions of the 5' and/or 3' untranslated region of IP cDNA. IP activity and levels of protein expression can be determined following the introduction, both singly and in combination, of these constructs into appropriate host cells. Following determination of the IP cDNA cassette yielding optimal expression in transient assays, this IP cDNA construct is transferred to a variety of expression vectors (including recombinant viruses), including but not limited to those for mammalian cells, plant cells, insect cells, oocytes, E. coli, and yeast cells.

Mammalian cell transfectants are assayed for both the levels of IP receptor activity and levels of IP protein by the following methods. Assessing IP receptor activity involves the direct introduction of a labelled ligand to the cells and determining the amount of specific binding of the ligand to the IP-expressing cells. Binding assays for receptor activity are known in the art (Frey et al., 1993, Eur. J. Pharmacol., 244, pp 239–250).

Levels of IP protein in host cells is quantitated by a variety of techniques including, but not limited to, immunoaffinity and/or ligand affinity techniques. IP-specific affinity beads or IP-specific antibodies are used to isolate $^{35}$S-methionine labelled or unlabelled IP protein. Labelled IP protein is analyzed by SDS-PAGE. Unlabelled IP protein is detected by Western blotting, ELISA or RIA assays employing IP specific antibodies.

Following expression of IP in a host cell, IP protein may be recovered to provide IP in active form, capable of binding IP-specific ligands. Several IP purification procedures are available and suitable for use. Recombinant IP may be purified from cell membranes by various combinations of, or individual application of standard separation techniques including but not limited to detergent solubilization, salt fractionation, ion exchange chromatography, size exclusion chromatography, hydroxylapatite adsorption chromatography and hydrophobic interaction chromatography.

In addition, recombinant IP can be separated from other cellular proteins by use of an immuno-affinity column made with monoclonal or polyclonal antibodies specific for full length nascent IP, or polypeptide fragments of IP.

Monospecific antibodies to IP are purified from mammalian antisera containing antibodies reactive against IP or are prepared as monoclonal antibodies reactive with IP using the technique of Kohler and Milstein, Nature 256:495–497 (1975). Monospecific antibody as used herein is defined as a single antibody species or multiple antibody species with homogenous binding characteristics for IP. Homogenous binding as used herein refers to the ability of the antibody species to bind to a specific antigen or epitope, such as those associated with the IP, as described above. IP specific antibodies are raised by immunizing animals such as mice, rats, guinea pigs, rabbits, goats, horses and the like, with an appropriate concentration of IP or a peptide derived from the sequence of the IP protein either with or without an immune adjuvant.

Preimmune serum is collected prior to the first immunization. Each animal receives between about 0.1 µg and about 1000 µg of IP or IP-related peptide associated with an acceptable immune adjuvant. Such acceptable adjuvants include, but are not limited to, Freund's complete, Freund's incomplete, alum-precipitate, water in oil emulsion containing Corynebacterium parvum and tRNA. The initial immunization consisted of the enzyme in, preferably, Freund's complete adjuvant at multiple sites either subcutaneously (SC), intraperitoneally (IP) or both. Each animal is bled at regular intervals, preferably weekly, to determine antibody titer. The animals may or may not receive booster injections following the initial immunization. Those animals receiving booster injections are generally given an equal amount of IP or IP-related peptide in Freund's incomplete adjuvant by the same route. Booster injections are given at about three week intervals until maximal titers are obtained. At about 7 days after each booster immunization or about weekly after a single immunization, the animals are bled, the serum collected, and aliquots are stored at about −20° C.

Monoclonal antibodies (mAb) reactive with IP or a peptide derived from the sequence of the IP protein are prepared by immunizing inbred mice, preferably Balb/c, with IP or IP-related peptide. The mice are immunized by the IP or SC route with about 1 µg to about 100 µg, preferably about 10 µg, of IP or IP-related peptide in about 0.5 ml buffer or saline incorporated in an equal volume of an acceptable adjuvant, as discussed above. Freund's complete adjuvant is preferred. The mice receive an initial immunization on day 0 and are rested for about three to about 30 weeks. Immunized mice are given one or more booster immunizations of about 1 to about 100 µg of IP in a buffer solution such as phosphate buffered saline by the intravenous (IV) route. Lymphocytes, from antibody positive mice, preferably splenic lymphocytes, are obtained by removing spleens from immunized mice by standard procedures known in the art. Hybridoma cells are produced by mixing the splenic lymphocytes with an appropriate fusion partner, preferably myeloma cells, under conditions which will allow the formation of stable hybridomas. Fusion partners may include, but are not limited to: mouse myelomas P3/NS1/Ag 4-1; MPC-11; S-194 and Sp 2/0, with Sp 2/0 being preferred. The antibody producing cells and myeloma cells are fused ha polyethylene glycol, about 1000 mol. wt., at concentrations from about 30% to about 50%. Fused hybridoma cells are selected by growth in hypoxanthine, thymidine and aminopterin supplemented Dulbecco's Modified Eagles Medium (DMEM) by procedures known in the art. Supernatant fluids are collected from growth positive wells on about days 14, 18, and 21 and are screened for antibody production by an immunoassay such as solid phase immunoradioassay (SPIRA) using IP or IP-related peptide as the antigen The culture fluids are also tested ha the Ouchterlony precipitation assay to determine the isotype of the mAb. Hybridoma cells from antibody positive wells are cloned by a technique such as the soft agar technique of MacPherson, Soft Agar Techniques, in Tissue Culture Methods and Applications, Kruse and Paterson, Eds., Academic Press, 1973.

Monoclonal antibodies are produced in vivo by injection of pristine primed Balb/c mice, approximately 0.5 ml per mouse, with about $2\times10^6$ to about $6\times10^6$ hybridoma cells about 4 days after priming. Ascites fluid is collected at approximately 8–12 days after cell transfer and the monoclonal antibodies are purified by techniques known in the art.

In vitro production of anti-IP mAb is carried out by growing the hybridoma in DMEM containing about 2% fetal calf serum to obtain sufficient quantities of the specific mAb. The mAb are purified by techniques known in the art.

Antibody titers of ascites or hybridoma culture fluids are determined by various serological or immunological assays which include, but are not limited to, precipitation, passive agglutination, enzyme-linked immunosorbent antibody (ELISA) technique and radioimmunoassay (RIA) techniques. Similar assays are used to detect the presence of IP in body fluids or tissue and cell extracts.

It is readily apparent to those skilled in the art that the above described methods for producing monospecific antibodies may be utilized to produce antibodies specific for IP polypeptide fragments, or full-length IP polypeptide.

IP antibody affinity columns are made by adding the antibodies to Affigel-10 (Biorad), a gel support which is pre-activated with N-hydroxysuccinimide esters such that the antibodies form covalent linkages with the agarose gel bead support. The antibodies are then coupled to the gel via amide bonds with the spacer arm. The remaining activated esters are then quenched with 1M ethanolamine HCl (pH 8). The column is washed with water followed by 0.23M glycine HCl (pH 2.6) to remove any non-conjugated antibody or extraneous protein. The column is then equilibrated in phosphate buffered saline (pH 7.3) together with appropriate membrane solubilizing such as detergents and the cell culture supernatants or cell extracts containing IP or IP fragments are slowly passed through the column. The column is then washed with phosphate buffered saline together with appropriate membrane solubilizing such as detergents until the optical density ($A_{280}$) falls to background, then the protein is eluted with 0.23M glycine-HCl (pH 2.6) together with appropriate membrane solubilizing such as detergents. The purified IP protein is then dialyzed against phosphate buffered saline together with appropriate membrane solubilizing agent, such as detergents.

One method suitable for the isolation of DNA encoding the prostaglandin receptor of the present invention involves the utilization of amino acid and/or DNA sequence information obtained from other G-protein-linked receptors. Since other prostaglandin receptors are known to be G-protein linked, certain regions or domains such as the transmembrane and/or cytoplasmic domains, are expected to have some degree of homology sufficient to produce a probe for the isolation of novel receptors.

Prostaglandins and leukotrienes are known to transduce their signals via G-protein-linked receptors. Distinct receptors for $PGH_2$/thromboxane $A_2$, $PGI_2$, $PGE_2$, $PGD_2$, PGF2a, $LTB_4$, and $LTD_4$ present in various tissues have been described. Some of the receptors have been solubilized and partially purified (Dutta-Roy, A. K. et al., (1987) JBC, 262, pp. 12685; Tsai, A. L. et al., (1989), JBC, 264, pp 61; Watanabe, T. el. al., (1990), JBC, 265, pp. 21237) and the human platelet $TXA_2$ receptor has been pad fled to apparent homogeneity (Ushikubi, F. et. al., (1989), JBC, 264, pp. 16496). The purified thromboxane receptor exhibited a very broad band on a SDS-polyacrylamide gel centered at appr. 57 kDa. Enough protein was obtained for partial sequence information.

An approach to the isolation of other eicosanoid receptor genes by homology screening was taken, with the assumption that these receptors are related in primary structure (Sugimoto, Y. et al., (1992), JBC, 267, pp. 6463). Since these receptors are of the G-protein-coupled receptor superfamily there are areas of homology which are likely to be found in the transmembrane region and in the cytoplasmic domains. Therefore, various known G-protein linked receptors related to the prostaglandin receptors may be utilized to provide DNA probes to regions of the receptor protein-encoding DNA sought, which is likely to have homology, such as the transmembrane region.

Using an antisense 16-fold degenerate 26 mer oligonucleotide based upon a stretch of nine amino acids in transmembrane domain VII of the published mouse $EP_2$ receptor amino acid sequence a human lung library was screened from which human IP cDNA clones were isolated. From two such cDNA clones one was constructed. This 1.417 kb cDNA clone encodes a 386-amino acid protein. This protein was designated as the IP receptor. Like many other G-protein coupled receptors the IP receptor shares several common features. Firstly, there is 1 potential N-linked glycosylation site at Asn7 in the putative extracellular amino terminus. Secondly, conserved cysteine residues are found in extracellular loops 1 and 2. There are serine residues, potential sites of protein kinase phosphorylation, in the C-terminus. The IP receptor possesses a conserved arginine (position 279) found in all known eicosanoid receptors within transmembrane seven. This region is the most highly conserved among the eicosanoid receptors.

The novel prostaglandin receptor of the present invention is suitable for use in an assay procedure for the identification of compounds which modulate the receptor activity. Modulating receptor activity, as described herein includes the inhibition or activation of the receptor and also includes directly or indirectly affecting the normal regulation of the receptor activity. Compounds which modulate the receptor activity include agonists, antagonists and compounds which directly or indirectly affect regulation of the receptor activity.

The prostaglandin receptor of the present invention may be obtained from both native and recombinant sources for use in an assay procedure to identify receptor modulators. In general, an assay procedure to identify prostaglandin receptor modulators will contain the prostaglandin receptor of the present invention, and a test compound or sample which contains a putative prostaglandin receptor modulator. The test compounds or samples may be tested directly on, for example, purified receptor protein whether native or recombinant, subcellular fractions of receptor-producing cells whether native or recombinant, and/or whole cells expressing the receptor whether native or recombinant. The test compound or sample may be added to the receptor in the presence or absence of a known labelled or unlabelled receptor ligand. The modulating activity of the test compound or sample may be determined by, for example, analyzing the ability of the test compound or sample to bind to the receptor, activate the receptor, inhibit receptor activity, inhibit or enhance the binding of other compounds to the receptor, modify receptor regulation, or modify an intracellular activity.

The identification of modulators of IP receptor activity are useful in treating disease states involving the IP receptor activity. Other compounds may be useful for stimulating or inhibiting activity of the receptor. Selective agonists or antagonists of the IP receptor may be of use in the treatment of diseases and disease states including, but not limited to, edema associated with intimation, pain response and fever, and may have utility in the inhibition of platelet aggregation and hence in the treatment of vascular diseases, prevention of post-injury blood clotting and rejection in organ transplantation and by-pass surgery, congestive heart failure, pulmonary hypertension, gangrene, Raynauds disease, bone

9 resorption, shock, and gastric acid secretion. Modulators may also be useful as cytoprotective agents. The isolation and purification of an IP-encoding DNA molecule would be useful for establishing the tissue distribution of IP receptors, studying changes in IP receptor expression in disease states, as well as establishing a process for identifying compounds which modulate IP receptor activity.

The following examples are provided for the purpose of illustrating the present invention without, however, limiting the same thereto.

EXAMPLE 1

Cloning of the IP cDNA

An antisense 16-fold degenerate 26mer oligonucleotide (designated oligo $EP_2$ d.o. VII(−)) [5'-TA(A,G)ATCCAGGG(A,G)TC(T,C)AGGATGGG(G,A)TT-3'] (SEQ.ID.NO.:1) based on the 9 amino acids (NPILDPWIY) (SEQ.ID.NO.:2) in transmembrane domain (TMD) VII of the mouse $EP_2$ receptor and highly conserved within the TP, $EP_1$, $EP_3$ and FP receptors was synthesized on a Model 380A DNA synthesizer (Applied Biosystems, Foster City, Calif.). The $^{32}P$-labeled oligo $EP_2$ d.o. VII(−) probe was used to screen human lung, thymus and small intestine λgt10 cDNA libraries (Clontech, Palo Alto, Calif.) using standard techniques (Sambrook et al., 1989, Molecular Cloning: A Laboratory Manual, 2nd Ed., Cold Spring Harbor Laboratory, Cold Spring Harbor, N.Y.). Positive phage clones from all three libraries were plaque purified and DNA was prepared by the plate lysate method (Sambrook et al., 1989, Molecular Cloning: A Laboratory Manual, 2nd Ed., Cold Spring Harbor Laboratory, Cold Spring Harbor, N.Y.). Phage DNA was digested with EcoRI and the resulting fragments were subcloned into the Bluescript vector pKS (Stratagene, La Jolla, Calif.). The T7 sequencing kit from Pharmacia (Bale d'Uffe, Canada) was used with KS and SK primers or primers generated from the determined sequences. Two clones in particular from the lung library, λhLc.6 and λhLc.11, when digested with EcoRI were found to contain inserts of sizes 1.3 kb (designated hLXR3-6, shown in FIG. 1) and 1.5 kb (designated hLXR3-11, shown in FIG. 2), respectively. The fragments were sequenced on both strands and cDNA hLXR3-11 was found to be extended by 72 bp at the 5'-end and 56 bp at the 3'-end when compared with hLXR3-6. hLXR3-11 was also found to contain a 24 nucleotide repeat which occurred in transmembrane domain (TMD) VII which would cause it to be increased by eight amino acids. pKS-hLXR3-11 was digested with SmaI and NcoI and a 0.4 kb fragment was purified and subsequently ligated into pKS-hLXR3-6 previously cut with EcoRV and NcoI in order to exchange the 5' end of hLXR3-6 for that of hLXR3-11 creating pKS-11/6hLXR3 and the hIP cDNA 11/6hLXR3 (FIG. 3).

The nucleotide sequence of 11/6hLXR3 (hIP) is shown in FIG. 3. The amino acid sequence for the encoded protein is shown in FIG. 4. The 1.417 kb fragment (IP; FIG. 3), when sequenced, was found to contain sequence homology to the mouse $EP_2$, human $EP_1$, $EP_3$ and thromboxane receptor cDNA and the putative heptahelical arrangement characteristic of G protein-coupled receptors, was evident. A long open reading frame (1158 bp) was identified which encodes a 386 amino acid polypeptide with a predicted relative molecular mass of 40,961. There are 56 bp of 5'-untranslated sequence and 203 bp of 3'-untranslated sequence.

10

EXAMPLE 2

Construction of the pcDNAIamp-11/6hLXR3 (hIP) expression vector (11/6hLXR3) which was subcloned into the EcoRI site of pcDNAIamp (Invitrogen, San Diego, Calif.). The correct orientation was verified by SphI digestion.

EXAMPLE 3

Cloning of the IP cDNA into E. coli Expression Vectors

Recombinant IP is produced in E. coli following the transfer of the IP expression cassette into E. coli expression vectors, including but not limited to, the pET series (Novagen). The pET vectors place IP expression under control of the tightly regulated bacteriophage T7 promoter. Following transfer of this construct into an E. coli host which contains a chromosomal copy of the T7 RNA polymerase gene driven by the inducible lac promoter, expression of IP is induced when an appropriate lac substrate (IPTG) is added to the culture. The levels of expressed IP are determined by the assays described above.

The cDNA encoding the entire open reading frame for IP is inserted into the NdeI site of pET 11 a. Constructs in the positive orientation are identified by sequence analysis and used to transform the expression host strain BL21. Transformants are then used to inoculate cultures for the production of IP protein. Cultures may be grown in M9 or ZB media, whose formulation is known to those skilled in the art. After growth to an approximate $OD_{600}=1.5$, expression of IP is induced with 1 mM IPTG for three hours at 37° C. IP receptor binding activity will be found in membrane fractions from these cells.

EXAMPLE 4

In Vivo Translation of Synthetic IP mRNA by Xenopus Oocyte Microinjection and Expression in Mammalian Cells IP cDNA constructs are ligated into in vitro transcription vectors (the pGEM series, Promega) for the production of synthetic mRNAs.

Synthetic mRNA is produced in sufficient quantity in vitro by cloning double stranded DNA encoding IP mRNA into a plasmid vector containing a bacteriophage promoter, linearizing the plasmid vector containing the cloned IP-encoding DNA, and transcribing the cloned DNA in vitro using a DNA-dependent RNA polymerase from a bacteriophage that specifically recognizes the bacteriophage promoter on the plasmid vector.

Various plasmid vectors are available containing a bacteriophage promoter recognized by a bacteriophage DNA-dependent RNA polymerase, including but not limited to plasmids pSP64, pSP65, pSP70, pSP71, pSP72, pSP73, pGEM-3Z, pGEM-4Z, pGEM-3Zf, pGEM-5Zf, pGEM-7Zf, pGEM-9Zf, and pGEM-11Zf, the entire series of plasmids is commercially available from Promega.

The double stranded IP-encoding DNA is cloned into the bacteriophage promoter containing vector in the proper orientation using one or more of the available restriction endonuclease cloning sites on the vector which are convenient and appropriate for cloning IP DNA. The vector with the ligated IP DNA is used to transform bacteria, and clonal isolates are analyzed for the presence of the vector with the 12P DNA in the proper orientation.

Once a vector containing the IP-encoding DNA in the proper orientation is identified and isolated, it is linearized by cleavage with a restriction endonuclease at a site downstream from, and without disrupting, the IP transcription unit. The linearized plasmid is isolated and purified, and used as a template for in vitro transcription of IP mRNA.

The template DNA is then mixed with bacteriophage-specific DNA-dependent RNA polymerase in a reaction mixture which allows transcription of the DNA template forming IP mRNA. Several bacteriophage-specific DNA-dependent RNA polymerases are available, including but not limited to T3, T7, and SP6 RNA polymerase. The synthetic IP mRNA is then isolated and purified.

It may be advantageous to synthesize mRNA containing a 5' terminal cap structure and a 3' poly A tail to improve mRNA stability. A cap structure, or 7-methylguanosine, may be incorporated at the 5'terminus of the mRNA by simply adding 7-methylguanosine to the reaction mixture with the DNA template. The DNA-dependent RNA polymerase incorporates the cap structure at the 5' terminus as it synthesizes the mRNA. The poly A tail is found naturally occurring in many cDNAs but can be added to the 3' terminus of the mRNA by simply inserting a poly A tail-encoding DNA sequence at the 3' end of the DNA template.

The isolated and purified IP mRNA is translated using either a cell-free system, including but not limited to rabbit reticulocyte lysate and wheat germ extracts (both commercially available from Promega and New England Nuclear) or in a cell based system, including but not limited to microinjection into Xenopus oocytes, with microinjection into Xenopus oocytes being preferred.

Xenopus oocytes are microinjected with a sufficient amount of synthetic IP mRNA to produce IP protein. The microinjected oocytes are incubated to allow translation of the IP mRNA, forming IP protein.

These synthetic mRNAs are injected into Xenopus oocytes (stage 5–6) by standard procedures [Gurdon, L. B. and Wickens, M. D. Methods in Enzymol. 101: 370–386, (1983)]. Oocytes are harvested and analyzed for IP expression as described below.

EXAMPLE 5 pcDNAIamp-IP expression in Xenopus oocytes

Oocytes were taken from adult females of *Xenopus laevis* using standard surgical procedure (Colman, A., 1984 In: Transcription and Translation—A Practical Approach, IRL Press). To remove follicle cells, oocytes were treated for 2–3 h with freshly made collagenase (2 mg/ml, type 2, Worthington Biochemical Corp., Freehold, N.J.) in $Ca^{2+}$-free ND96 solution (ND96 in mM: NaCl 96, KCl 2, $MgCl_2$ 1, HEPES 5, Na-pyruvate 2.5, theophylline 0.5, gentamicin 50 mg/ml, +1.8 $CaCl_2$, pH 7.6). Defolliculated stage 5–6 oocytes were selected and maintained in ND96 solution. Oocyte nuclei were injected with 1.6 ng of pcDNAIamp-IP plus 2.5 ng of pcDNAIamp-CFTR and then incubated at 18° C. for 48 h before challenge with agonist. CFTR (cystic fibrosis transmembrane regulator, a cAMP dependent $Cl^-$ channel) was co-expressed with IP receptor in these oocytes and served as a reporter of changes in intracellular cAMP levels. Functional activity was determined by measurement of Iloprost-induced CFTR-mediated $Cl^-$ current. An oocyte was placed in a 0.5 ml perfusion chamber and voltage clamped at −60 mV (with microelectrodes of 0.5–2.0 MW resistance filled with 3M KCl) using a Turbo TEC 01C amplifier (NPI Instruments, Germany). Ligand-containing solution was perfused and the current response was recorded.

Figure 5A:
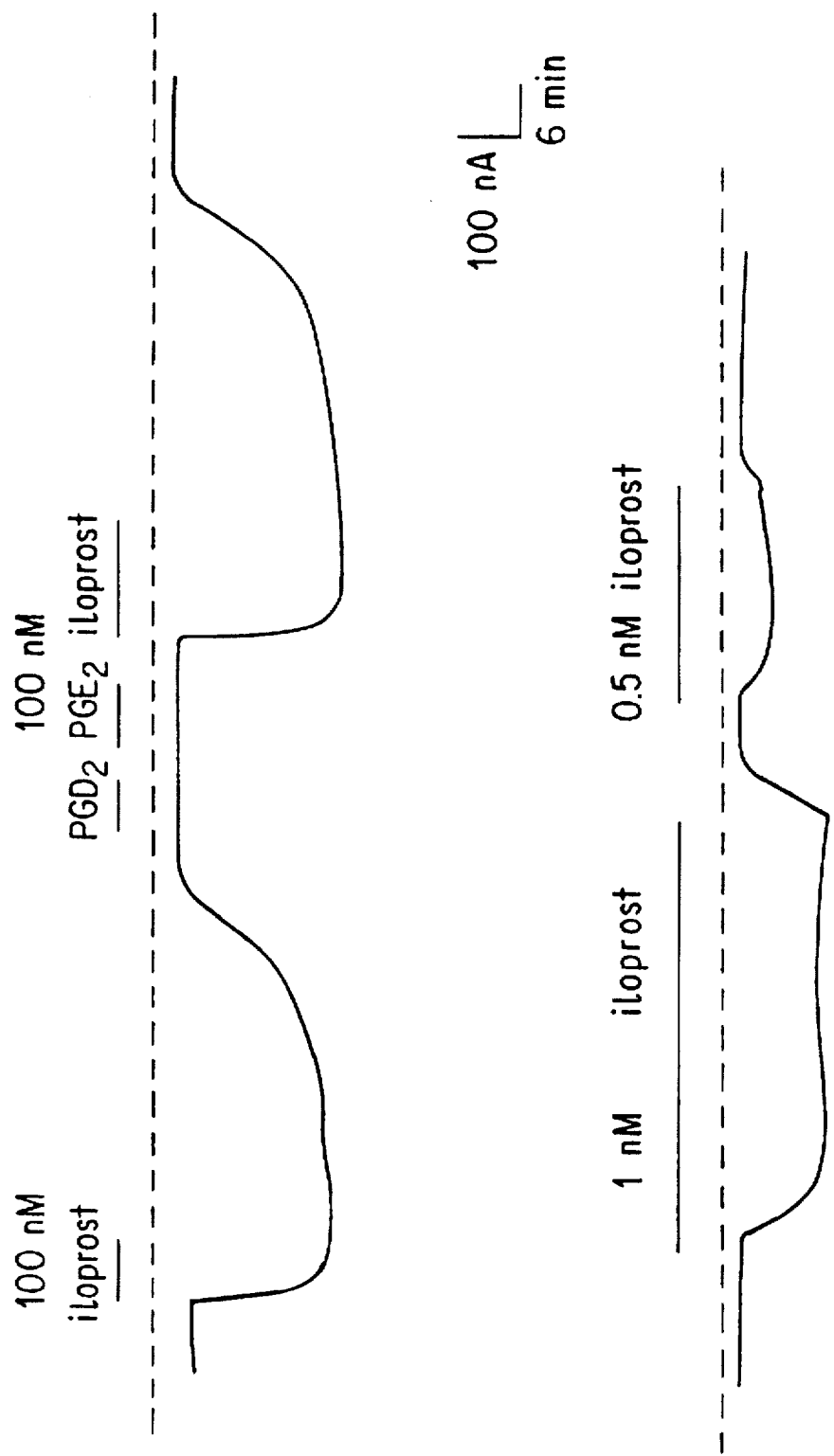
FIG. 5—Expression of the prostaglandin $I_2$ receptor in IP cDNA-injected Xenopus oocytes is shown. Panel A shows iloprost induced CFTR-mediated $Cl^-$ current evoked by bath perfusion of 1–100 nM iloprost and not by $PGE_2$ or $PGD_2$ in an oocyte that was co-injected with 2.6 ng pcDNAIamp-CFTR and 1 ng pcDNAIamp-11/6hLXR3 (hIP cDNA). Panel B shows the absence of endogenous IP receptors in oocytes. Oocytes were injected with CFTR cDNA and challenged with 100 nM iloprost, $PGE_2$, $PGD_2$ and 3 mM IBMX. The broken line represents the zero current level.

Perfusion of 1–100 nM iloprost agonist, resulted in prominent current responses in oocytes injected with pcDNAIamp-IP plus pcDNAIamp-CFTR confirming that this clone encodes a functional IP receptor that is coupled to the cAMP signalling pathway (FIG. 5, Panel A). The response to 100 nM $PGD_2$ or $PGE_2$ was not detectable as expected for the IP receptor. This rank order of potency is consistent with that reported for the IP receptor [Coleman, et al., 1990. Comprehensive Medicinal Chemistry (Hansch, C., Samroes, P. G., Taylor, J. B., and Emmett, J. C., Eds) Vol. 3, pp. 643–714, Pergamon, Press, Oxford]. In control (CFTR alone injected) oocytes no responses to iloprost, $PGE_2$ and $PGD_2$ were observed despite high levels of CFTR expression as indicated by the effects of IBMX (FIG. 5, Panel B).

EXAMPLE 6

Cloning of IP cDNA into a Mammalian Expression Vector

IP cDNA expression cassettes are ligated at appropriate restriction endonuclease sites to the following vectors containing strong, universal mammalian promoters: pBC12BI [Cullen, B. R. Methods in Enzymol. 152:684–704 1988], and pEE12 (CellTech EP 0 338,841) and its derivatives pSZ9016-1 and p9019. p9019 represents the construction of a mammalian expression vector containing the hCMVIE promoter, polylinker and SV40 polyA element with a selectable marker/amplification system comprised of a mutant gene for dihydrofolate reductase (mDHFR) (Simonsen, C. C. and Levinson, A. D. Proc. Natl. Acad. Sci U.S.A. 80:2495–2499 [1983]) driven by the SV40 early promoter. An SV40 polyadenylation sequence is generated by a PCR reaction defined by primers 13978-120 and 139778-121 using pD5 (Berker and Sharp, Nucl. Acid Res. 13:841–857 [1985]) as template. The resulting 0.25 Kb PCR product is digested with ClaI and SpeI and ligated into the 6.7 Kb fragment of pEE12 which had been likewise digested. The resultant plasmid is digested with BglII and SfiI to liberate the 3' portion of the SV40 early promoter and the GScDNA from the vector. A 0.73 Kb SfiI-XholI fragment isolated from plasmid pFR400 (Simonsen, C. C. and Levinson, A. D. Proc. Natl. Acad. Sci U.S.A. 80: 2495–2499 [1983]) is ligated to the 5.6 Kb vector described above, reconstituting the SV40 early promoter, and inserting the mdHFR gene. This plasmid is designated p9019. pSZ9016-1 is identical to p9019 except for the substitution of the HIV LTR for the huCMVIE promoter. This vector is constructed by digesting p9019 with XbaI and MluI to remove the huCMVIE promoter. The HIV LTR promoter, from residue −117 to +80 (as found in the vector pCD23 containing the portion of the HIV-1 LTR (Cullen, Cell 46:973 [1986]) is PCR amplified from the plasmid pCD23 using oligonucleotide primers which appended to the ends of the product the MluI and SpeI restriction sites on the 5' side while Hind III and Xba I sites are appended on the 3' side. Following the digestion of the resulting 0.2 kb PCR product with the enzymes MluI and Xba I the fragment is agarose gel-purified and ligated into the 4.3 Kb promoterless DNA fragment to generate the vector pSZ9016-1.

Cassettes containing the IP cDNA in the positive orientation with respect to the promoter are ligated into appropriate restriction sites 3' of the promoter and identified by restriction site mapping and/or sequencing. These cDNA expression vectors are introduced into various host cells including, but not limited to: COS-7 (ATCC# CRL1651), CV-1 [Sackevitz et al., Science 238:1575 (1987)], 293, L cells (ATCC# CRL6362)] by standard methods including but not limited to electroporation or chemical procedures (cationic liposomes, DEAE dextran, calcium phosphate). Transfected cells and cell culture extracts can be harvested and analyzed for IP expression as described below.

All of the vectors used for mammalian transient expression can be used to establish stable cell lines expressing IP. Unaltered IP cDNA constructs cloned into expression vectors will be expected to program host cells to make intracellular IP protein. The transfection host cells include, but are not limited to, CV-1 [Sackevitz et al., Science 238: 1575

(1987)], tk-L [Wigler, et al. Cell 11:223 (1977)], NS/O, and dHFr-CHO [Kaufman and Sharp, J. Mol. Biol. 159: 601, (1982)].

Co-transfection of any vector containing IP cDNA with a drug selection plasmid including, but not limited to G418, aminoglycoside phosphotransferase, pLNCX [Miller, A. D. and Rosman G. J. Biotech News 7:980–990 (1989)]; hygromycin, hygromycin-B phosphotransferase, pLG90 [Gritz. L. and Davies, J., GENE 25:179 (1983)]; APRT, xanthine-guanine phosphoribosyl-transferase, pMAM (Clontech) [Murray, et all., Gene 31:233 (1984)] will allow for the selection of stably transfected clones. Levels of IP are quantitated by the assays described above.

IP cDNA constructs are ligated into vectors containing amplifiable drug-resistance markers for the production of mammalian cell clones synthesizing the highest possible levels of IP. Following introduction of these constructs into cells, clones containing the plasmid are selected with the appropriate agent, and isolation of an over-expressing clone with a high copy number of the plasmid is accomplished by selection in increasing doses of the agent. The following systems are utilized: the 9016 or the 9019 plasmid containing the mutant DHFR gene [Simonson, C. and Levinson, A., Proc. Natl. Acad. Sci. U.S.A. 80:2495 (1983)], transfected into DHFR- CHO cells and selected in methotrexate; the pEE12 plasmid containing the glutamine synthetase gene, transfected into NS/O cells and selected in methionine sulfoximine (CellTech International Patent Application 2089/10404); and 9016 or other CMV promoter vectors, co-transfected with pDLAT-3 containing the thymidine kinase gene [Colbere and Garopin, F., Proc. Natl. Acad. Sci. 76:3755 (1979)] in APRT and TK deficient L cells, selected in APRT (0.05 mM azaserine, 0.1 mM adenine, 4 ug/ml adenosine) and amplified with HAT (100 uM hypoxanthine, 0.4 uM aminopterin, 16 uM thymidine).

EXAMPLE 7

Expression of the IP receptor in COS-M6 cells and [$^3$H] iloprost binding assays The recently cloned human prostaglandin $I_2$ (IP) receptor was subcloned into the pcDNAlamp plasmid (Invitrogen) and transfected into COS-M6 cells using the DEAE-dextran method. The cells were maintained in culture for 72 h, then harvested and membranes prepared by differential centrifugation (1000 ×g for 10 min, then 100,000 ×g for 30 min) following lysis of the cells by nitrogen cavitation. [$^3$H] iloprost binding assays were performed in 10 mM MES/KOH pH 6.0, containing 1.0 mM EDTA, 10 mM $MnCl_2$, 4 nM [$^3$H]iloprost and 60 µg of protein from the 100,000×g membrane fraction. Incubations were conducted for 45 min at 30° C. prior to separation of the bound and free radioligand by rapid filtration through Batman GF/B filters pre-soaked at 4° C. in washing buffer (10 µM MES/KOH (pH 6.0) containing 0.01% bovine serum albumin). The filters were washed with approximately 16 ml of washing buffer and the residual [$^3$H]iloprost bound to the filter was quantified by liquid scintillation counting. Specific binding was defined as the difference between total binding and non-specific binding, determined in the presence of 2 µM iloprost.

The cloned human IP receptor was transfected into COS-M6 cells and [$^3$H]iloprost binding assays were performed with membranes prepared from the transfected cells. The most effective competing ligand was iloprost, the metabolically stable prostacyclin mimetic which displayed an $IC_{50}$ value of 4.0±0.14 nM. The related prostacyclin analog carbacyclin was 100-fold less potent with an $IC_{50}$ value of 431±71 nM. $PGE_2$ and $PGF_{2\alpha}$ were considerably less effective as competing ligands with $IC_{50}$ values around 10 µM, while $PGD_2$ and the thromboxane analog U46619 were essentially inactive in competition for [$^3$H]iloprost specific binding to the hIP receptor at a concentration of 30 µM. The rank order of affinity for prostaglandins and related synthetic analogs at the hIP receptor was therefore: iloprost >>carbacyclin >> $PGE_2$>$PGF_{2\alpha}$=$PGD_2$=U46619. This rank order of potency has been predicted for the IP receptor from previous pharmacological studies.

EXAMPLE 8

Cloning of IP cDNA into a Baculovirus Expression Vector for Expression in Insect Cells Baculovirus vectors, which are derived from the genome of the AcNPV virus, are designed to provide high level expression of cDNA in the Sf9 line of insect cells (ATCC CRL# 1711). Recombinant baculoviruses expressing IP cDNA are produced by the following standard methods (In Vitrogen Maxbac Manual): the IP cDNA constructs are ligated downstream of the polyhedrin promoter in a variety of baculovirus transfer vectors, including the pAC360 and the pBlueBac vector (In Vitrogen). Recombinant baculoviruses are generated by homologous recombination following co-transfection of the baculovirus transfer vector and linearized AcNPV genomic DNA [Kilts, P. A., Nuc. Acid. Res. 18:5667 (1990)] into Sf9 cells. Recombinant pAC360 viruses are identified by the absence of inclusion bodies in infected cells (Summers, M. D. and Smith, G. E., Texas Agriculture Exp. Station Bulletin No. 1555) and recombinant pBlueBac viruses are identified on the basis of b-galactosidase expression (Vialard, et al. 1990, J. Virol., 64, pp 37–50). Following plaque purification and infection of sf9 cells with IP recombinant baculovirus, IP expression is measured by the assays described above.

The cDNA encoding the entire open reading frame for IP is inserted into the BamHI site of pBlueBacII. Constructs in the positive orientation with respect to the polyhedrin promoter are identified by sequence analysis and used to transfect Sf9 cells in the presence of linear AcNPV wild type DNA.

Authentic, active IP is found associated with the membranes of infected cells. Membrane preparations are prepared from infected cells by standard procedures.

EXAMPLE 9

Cloning of IP cDNA into a yeast expression vector

Recombinant IP is produced in the yeast S. cerevisiae following the insertion of the optimal IP cDNA construct into expression vectors designed to direct the intracellular expression of heterologous proteins. For intracellular expression, vectors such as EmBLyex4 or the like are ligated to the IP cistron [Rinas, U. et al., Biotechnology 8: 543–545 (1990); Horowitz B. et al., J. Biol. Chem. 265:4189–4192 (1989)]. The levels of expressed IP are determined by the assays described above.

EXAMPLE 10

Purification of Recombinant IP

Recombinantly produced IP may be purified by antibody affinity chromatography.

IP antibody affinity columns are made by adding the anti-IP antibodies to Affigel-10 (Biorad), a gel support which is pre-activated with N-hydroxysuccinimide esters such that the antibodies form covalent linkages with the agarose gel bead support. The antibodies are then coupled to the gel via amide bonds with the spacer arm. The remaining activated esters are then quenched with 1M ethanolamine HCl (pH 8). The column is washed with water followed by 0.23M glycine HCl (pH 2.6) to remove any non-conjugated antibody or extraneous protein. The column is then equilibrated in phosphate buffered saline (pH 7.3) together with appropriate membrane solubilizing agents such as detergents and the cell culture supernatants or cell extracts containing solubilized IP is slowly passed through the column. The column is then washed with phosphate-buffered saline together with detergents until the optical density (A280) falls to background, then the protein is eluted with 0.23M glycine-HCl (pH 2.6) together with detergents. The purified IP protein is then dialyzed against phosphate buffered saline together with detergents.

What is claimed is:

1. A human prostaglandin receptor protein IP free from other human proteins which comprises the amino acid sequence set forth in SEQ ID NO:3.

2. A human prostaglandin receptor protein IP of claim 1 obtained from a recombinant host cell transformed or transfected with a DNA molecule encoding the human prostaglandin receptor protein IP.

3. A membrane preparation comprising the human prostaglandin receptor protein of claim 1, wherein said membrane preparation is obtained from a recombinant host cell transformed or transfected with a DNA molecule encoding the human prostaglandin receptor protein IP.

4. A human prostaglandin receptor protein IP free from other human proteins which consists of the amino acid sequence set forth in SEQ ID NO:3.

5. A human prostaglandin receptor protein IP of claim 4 obtained from a recombinant host cell transformed or transfected with a DNA molecule encoding the human prostaglandin receptor protein IP.

6. A membrane preparation comprising the human prostaglandin receptor protein of claim 4, wherein said membrane preparation is obtained from a recombinant host cell transformed or transfected with a DNA molecule encoding the human prostaglandin receptor protein IP.

* * * * *